US008894927B2

(12) United States Patent  (10) Patent No.: US 8,894,927 B2
Finch  (45) Date of Patent: Nov. 25, 2014

(54) SHOWER STERILISATION SYSTEM AND METHOD OF USE THEREOF

(71) Applicant: Stephen Finch, Waterside (GB)

(72) Inventor: Stephen Finch, Waterside (GB)

(73) Assignee: Omnia-Klenz Ltd., Manchester (GB)

( * ) Notice: Subject to any disclaimer, the term of this patent is extended or adjusted under 35 U.S.C. 154(b) by 222 days.

(21) Appl. No.: 13/724,325

(22) Filed: Dec. 21, 2012

(65) Prior Publication Data

US 2013/0177475 A1    Jul. 11, 2013

Related U.S. Application Data

(63) Continuation of application No. PCT/GB2011/051214, filed on Jun. 27, 2011.

(30) Foreign Application Priority Data

Jun. 28, 2010 (GB) .................................. 1010808.2

(51) Int. Cl.
A61L 2/18 (2006.01)
A01N 33/04 (2006.01)
E03C 1/046 (2006.01)
B05B 7/24 (2006.01)

(52) U.S. Cl.
CPC . A61L 2/18 (2013.01); A01N 33/04 (2013.01); E03C 1/046 (2013.01); B05B 7/2462 (2013.01)
USPC .................................. 422/28; 239/310; 4/615

(58) Field of Classification Search
CPC ....................................................... A61L 2/18
USPC .......................... 422/28; 239/302, 310; 4/615
See application file for complete search history.

(56) References Cited

U.S. PATENT DOCUMENTS

| | | | |
|---|---|---|---|
| 1,668,802 | A | 5/1928 | Cantrell |
| 3,460,562 | A | 8/1969 | Moulder |
| 3,847,354 | A | 11/1974 | Lemond |
| 6,395,172 | B1 | 5/2002 | Koike |
| 6,647,566 | B1 | 11/2003 | Wang |
| 2002/0070293 | A1 | 6/2002 | Ti |
| 2007/0113892 | A1 | 5/2007 | Chiriac et al. |
| 2007/0119980 | A1 | 5/2007 | Somerfield et al. |
| 2007/0210185 | A1 | 9/2007 | Paoluccio |

FOREIGN PATENT DOCUMENTS

| | | |
|---|---|---|
| DE | 2510381 | 9/1976 |
| DE | 199016641 | 4/1991 |
| DE | 202007011127 | 11/2007 |
| EP | 0375367 | 6/1990 |
| EP | 1518607 | 3/2005 |
| FR | 2264583 | 10/1975 |
| FR | 2620470 | 3/1989 |
| FR | 2721834 | 1/1996 |
| GB | 1465727 | 3/1977 |
| JP | 11071210 | 3/1999 |
| WO | WO 02/50378 | 6/2002 |
| WO | WO 2007/032918 | 3/2007 |
| WO | WO 2008/030458 | 3/2008 |
| WO | WO 2009/098571 | 8/2009 |

Primary Examiner — Sean E Conley
(74) Attorney, Agent, or Firm — Woodard, Emhardt, Moriarty, McNett & Henry LLP

(57) ABSTRACT

A shower sterilization system is provided. The system comprises shower apparatus including water supply means (2), a shower head (6) and shower conduit means (4) connecting the shower head to the water supply means. An applicator device (16) is located between the water supply means and the shower head for receiving a sterilization or biocidal composition in use and allowing said sterilization or biocidal composition to be delivered to one or more parts of said shower apparatus.

15 Claims, 6 Drawing Sheets

SHOWER STERILISATION SYSTEM AND METHOD OF USE THEREOF

REFERENCE TO RELATED APPLICATIONS

This application is a continuation of PCT/GB2011/051214, filed 27 Jun. 2011, which is hereby incorporated by reference. This application claims priority from Patent Application No. GB 1010808.2, filed 28 Jun. 2010, which is hereby incorporated by reference.

The invention to which this application relates is a shower sterilisation system and method of use thereof.

In recent years there have been a number of high profile incidents where the spread of Legionnaires' disease in particular has caused great concern for public health and in some cases susceptible individuals have died as a result of contacting the disease (as for example reported on the BBC News website, at http://news.bbc.co.uk/go/pr/fr/-/1/hi/england/somerset/5256926.stm). The generally accepted mechanism for the spread of this disease is via the very fine particulate water mists/aerosols released from contaminated cooling towers or other facilities where aerosols can be produced and can contact personnel. A number of investigations have been carried out in the US and elsewhere to investigate the occurrence of microbiological contamination in domestic shower systems in particular and the presence of a number of potentially problematic species have been identified in a wide range of analyses from showers located in many different locations, and analyses carried out in the UK have yielded similar results.

One species frequently identified is *Mycobacterium avium* which is a particularly difficult bacterium to kill under normal circumstances. In addition, there are a number of other bacterial species that have been identified as being transferred via the aerosol route, such as *Legionella pneumophila*, which can seriously aggravate respiratory diseases particularly in vulnerable members of the population.

Whilst the exposure of the general public to aerosols from contaminated cooling towers will always be a potential issue, there are strict procedures laid down by the Health and Safety Executive (HSE) to treat, control, monitor, and report in a detailed manner all aspects of the treatment to control *Legionella* and other bacterial species in industrial cooling systems.

However, another widespread potential problem area of exposure for the general public is the daily use of showers which, by definition, produce aerosols which can easily allow fine water particles to be introduced into the respiratory tracts of the individuals showering. In fact, HSE document L8 which summarises the procedures to be applied in the control of *Legionella pneumophila* acknowledges the risk from showers and recommends that all shower systems in commercial and industrial facilities are treated with a high level of halogen release product, such as chlorine dioxide, on a regular basis.

Unfortunately the frequency proposed in the L8 guidelines of a quarterly treatment of each showerhead is largely influenced by the impracticality of the current procedure. In addition, it has been reported that *Mycobacteria* are resistance to chlorine treatment, possibly due to biofilm formation which provide protection to the bacteria from such treatment. The establishment of a bio-film on internal surfaces of shower apparatus is typically caused by a build up of calcium carbonate scale thereon from the water supply. The bacteria that are able to survive on this bio-film are rapidly re-inoculated back into any water that is left standing in the shower apparatus when the shower is not in use, such as in the shower hose or shower head. When the shower is switched back on, the bacteria are released in the water or as aerosols from the shower head. In particular, the aerosols are contaminated with particles of the biofilm containing the bacteria as a result of the biofilm being stripped from the internal surfaces of the apparatus caused by the turbulence of the water flowing through the apparatus.

While it is possible to use more aggressive treatments against bacterial growth, in an industrial setting the guidelines suggest that the plant is shut down while disinfection takes place as typically chemicals are provided in the header tank so that the whole system can be flushed through. These procedures by their very nature are involved and time consuming and, as a result, the potential exists for them to be difficult to effectively supervise and control to ensure that the optimum performance is routinely achieved.

As domestic showers have been shown to be the source of disease causing bacteria, and the currently available treatments are impractical, carried out too infrequently and/or are not effective in many situations (particularly the domestic environment), an aim of the present invention is to provide a shower sterilisation system that allows a simple and safe method of delivering an anti-microbial or sterilisation composition into shower apparatus to be established. A further aim of the invention is to establish a simple and effective method of cleaning shower apparatus to encourage frequent treatment of the apparatus using an anti-microbial or sterilisation composition, such that greater control of the build up of microbiological activity in the shower lines and head, and hence greater levels of overall protection, can be provided.

In one aspect of the present invention there is provided a shower sterilisation system, said system comprising shower apparatus including water supply means, a shower head and shower conduit means connecting the shower head to the water supply means, and an applicator device located between the water supply means and the shower head for receiving a sterilisation or biocidal composition in use and allowing said sterilisation or biocidal composition to be delivered to one or more parts of said shower apparatus.

The shower sterilisation system of the present invention allows a sterilisation or biocidal composition, or any other suitable composition, to be easily and effectively delivered to one or more parts of the shower apparatus to sterilise or clean the same.

Preferably the applicator device comprises a housing including inlet means and/or outlet means for allowing the flow of water from the shower apparatus therethrough in use.

Preferably the applicator device includes receiving means located in or forming part of the housing for receiving the sterilisation composition in use.

The housing and/or the receiving means of the applicator device preferably includes attachment means and/or access means to allow the composition to be placed in the receiving means in use.

Preferably the inlet and/or outlet means are provided with connection means for allowing connection of the applicator device to the shower apparatus in use.

The shower conduit means is typically any type of conduit, channel, tubing, hose, pipe and/or the like that allows water to flow therethrough from the water supply means to the shower head. The shower head is typically the portion of the shower apparatus from which the water is dispensed onto a user in use.

The applicator device can be attached, detachably attached or integrally formed with the shower apparatus.

In a further aspect of the present invention, there is provided an applicator device for delivering a composition to shower or fluid flow apparatus, said applicator device including;

a housing including inlet means and/or outlet means;

receiving means located in or forming part of the housing for receiving a composition in use;

the housing and/or the receiving means having attachment means and/or access means to allow the composition to be placed in the receiving means in use;

wherein the inlet and/or outlet means are provided with connection means for allowing connection of the applicator device to the shower or fluid flow apparatus in use.

The applicator device of the present invention allows effective delivery of a composition for cleaning or treating fluid flowing through the apparatus or one or more interior surfaces of the shower apparatus, fluid flow apparatus or other apparatus with which it is connected to in use. The applicator device can be retrofitted to existing shower or fluid flow apparatus, can be integrally formed therewith, attached to detachably attached to and/or the like. The composition is preferably a cleaning composition, such as a biocidal or sterilisation composition, an acidic sequestering composition and/or the like.

In one embodiment the receiving means defines an inner portion in fluid communication with an outer portion. Typically the inlet and outlet means are in respective fluid communication with the inner portion and the outer portion.

Preferably the inner portion includes a mesh, one or more apertures and/or the like to allow fluid communication between the inner and outer portions of the receiving means.

In one embodiment the receiving means can be in the form of a basket or container for containing or supporting the composition in use. Alternatively, the receiving means can be a cavity defined within the housing with delimiting means to separate the cavity of the receiving means from the remainder of the housing. The delimiting means can be filter means and/or the like. In either embodiment the basket, container or cavity is in fluid communication with the shower apparatus or fluid flow apparatus with which the applicator device is fitted to in use.

The inlet and/or outlet means preferably include at least one opening defined therein for the flow of fluid therethrough in use. In one embodiment separate inlet and outlet means are provided. In an alternative embodiment combined inlet and outlet means are provided.

The applicator device is typically in fluid communication with one or more parts of the shower apparatus. Preferably at least one fluid flow channel defined in the applicator device is substantially aligned with a fluid flow channel defined in the shower apparatus.

Preferably the applicator device is located between the water supply unit and the shower conduit means of the shower apparatus.

In one embodiment the applicator device is connected or provided substantially in-line with one or more parts of the shower apparatus through which fluid flows in use. Thus fluid or water flows from the water supply unit to the shower conduit means and head via the applicator device. The fluid flow allows any composition contained within the receiving means of the applicator device to be released into the water supply or fluid flow and pass out of the shower apparatus through the shower conduit and/or shower head.

Preferably the water flow channel of the applicator device and water flow channel of the part of the shower apparatus with which it is fitted to are substantially coaxially arranged. Thus, in one embodiment the longitudinal axis of the applicator device or channel defined in the applicator device is substantially parallel with and aligned with the longitudinal axis of the shower apparatus or channel defined in the shower apparatus with which it is connected to in use.

Typically one end of the shower conduit means is provided with a female screw thread for connection to a male screw thread on the water supply unit or means. Likewise, the shower head and the other end of the shower conduit means may be provided with opposite male/female screw threads to allow connection therebetween.

In one embodiment the connection means include one or more screw threads extending from, provided on or associated with the housing of the applicator device.

Preferably the screw threads of the connection means are both male, and therefore suitable for being received by the female screw thread of the shower conduit means to allow connection therebetween in use.

The connection means could include any or any combination of one or more screw threads, friction fit, push fit and locking connection, inter-engaging members, one or more teeth, protruding lug or pin members, quick-release fittings, twist-lock connections and/or the like.

In one embodiment adapter means are provided to allow connection between the shower apparatus and the applicator device. In one embodiment the adapter means includes a tube or conduit provided with screw threads at one or both ends, such as for example female screw threads. Therefore the male screw thread of the applicator device in one embodiment can be connected to the male screw thread of the water supply unit via the adapter means.

Preferably the adapter means engage the connection means of the applicator device to one or more parts of the shower or fluid flow apparatus in use.

Typically the screw threads are configured to half-inch British Standard Pipe (BSP).

In one embodiment the receiving means includes filtration means, typically capable of filtering the fluid flowing between the inner and outer portions or passing through the receiving means. Thus, in one embodiment, the filtration means defines the inner and outer portions or delimiting means of the receiving means.

In one embodiment the filtration means is a mesh, screen or gauze. Preferably the mesh or gauze is formed from plastic, metal or a metal based material.

In one embodiment the filtration means extends or is arranged substantially perpendicular to the direction of fluid flow through the apparatus or to a central longitudinal axis defined through the aperture of the inlet and/or outlet means. Preferably the receiving means and/or housing is substantially circular in cross-section. Typically the filtration means is substantially concentric with the receiving means and/or channel defined through the housing of the applicator device through which fluid flows in use.

In a further embodiment the filtration means extends across at least a portion of the housing between the inlet and outlet means to filter liquid or fluid flowing therebetween.

In one embodiment the housing is substantially Y-shaped or includes an outwardly protruding branch or arm portion from a main body portion to allow insertion of the composition therein in use. The branch or arm portion can be in fluid communication with the remainder of the housing or main body portion interior so that composition can pass into the water flowing through the housing in use.

Typically the composition is locatable in the inner portion or cavity of the receiving means, such that the filtration means of the receiving means retains any insoluble material, such as for example any PVA material where used.

Typically the applicator device is arranged to allow liquid or fluid to flow through the inlet means to the outlet means via the filtration means. Further typically in one embodiment the applicator device is arranged to allow liquid or fluid to flow through the inlet means into the inner portion, from the inner portion to the outer portion via the filtration means, and out from the outer portion via the outlet means. Liquid or fluid may then flow into a shower hose, conduit, pipe and/or the like connected to the outlet means.

In one embodiment the receiving means is detachably connected to the housing via attachment means. The attachment means can include any or any combination of one or more screw threads, friction fit, inter-engaging members, one or more clips, ties, screws and/or the like. Thus the receiving means can be removed to insert, remove and/or replace the composition therein in use.

In one embodiment the housing includes an access opening, and preferably in addition to one or more apertures of the inlet and/or outlet means, defined in a wall of the housing. The access opening allows user access to the interior of the housing and/or receiving means and preferably to the interior channel or cavity of the housing or receiving means through which fluid flows in use without having to remove the housing and/or receiving means from the apparatus. Preferably the composition can be located in the receiving means through the access opening of the housing.

Preferably closure means are provided for closing the access opening in use. The closure means are typically movable between an open position, wherein access to the access opening is possible, and a closed position, wherein the access opening is closed.

Preferably the closure means provides a substantially water tight sealing of the access opening when in a closed position to prevent fluid flowing through the applicator device from flowing through the access opening in the closed position.

The closure means can be pivotably, rotatable, slidably movably mounted on the housing and/or the like to allow movement of the closure means between the open and closed positions.

In one embodiment the closure means is slidably mounted on the housing and the closure means are maintained in the closed position by a rotatable nut or locking member.

In one embodiment the closure means is a slidable sleeve member mounted on the housing.

Preferably rotation of the nut or locking member in a direction away from the access opening allows the closure means to move from the closed position to an open position. Rotation of the nut or locking member in an opposite direction moves the closure means from an open position to a closed position.

In upright or vertical hard piped systems fitted with 'drain down' facilities, the applicator device can be fitted with a non-return ball valve which enables a column of water to be maintained in the fixed pipe even when the water flow is stopped and the 'drain down' valve automatically opens.

The applicator device is preferably used for the delivery of a chemical composition, such as an antimicrobial composition, a biocidal or sterilisation composition and/or acid sequestering composition, into the shower apparatus or fluid flow apparatus.

The composition for use with the applicator device can be in the form of a liquid, tablet, gel or powder. Typically the chemical composition is substantially soluble in water.

In one embodiment the composition is contained within a container, sachet, capsule or bag.

In one embodiment the container, sachet, capsule or bag is made of a soluble material, such as for example a soluble plastic material or film. Preferably the soluble material includes or comprises poly(vinyl alcohol or PVA).

In one embodiment the chemical composition includes a chemical carrier and preferably the chemical carrier is substantially or wholly non-aqueous (preferably below 5% aqueous content and preferably 0% aqueous content), such that it does not result in dissolution of the soluble container material before the required time in one embodiment.

In one embodiment the chemical carrier is or includes an alkylene glycol, such as hexylene glycol, in which the chemical may be soluble but the soluble plastic does not dissolve.

Preferably the alkylene glycol is provided in an amount of between 10-100% by weight of the final composition, and further preferably 50-100%.

Preferably the chemical composition includes any or any combination of antimicrobial, biocidal, descaling, chelating, sterilisation and/or other cleaning or treating components.

In one embodiment the chemical composition is a biocidal or sterilisation composition and includes a biocidal active component. Preferably the biocidal active component is N-(3-aminopropyl)-N-dodecylpropane-1,3-diamine (Lonzabac 12.100; CAS No. 2372-82-9; Lonza Ltd). Lonzabac 12 is registered for use as a biocide in various countries including the UK, Europe, and the US at concentrations of 0.5%, and is effective against *Legionella, Mycobacteria*, Hepatitis and HIV down to concentrations of 0.05%.

Preferably the biocidal active component is used in the composition in an amount of 1-5% by weight of the final composition.

Preferably the biocidal or sterilisation composition includes an alkyl alkoxylate. Preferably the alkyl alkoxylate is used in the composition in an amount of 2-10% by weight of the final composition. The alkyl alkoxylate typically acts as a wetting agent. Other wetting agents could be used.

In one embodiment the composition is an acid sequestering composition for removing calcium carbonate or precipitated hardness scale from the interior surfaces of the fluid flow apparatus or shower apparatus. This contributes to the removal of or cleaning of the 'key' to which a 'bio-film' layer may successfully adhere and build up. Preferably the composition includes an acid or organic acid, such as for example phosphonic acid.

Preferably the acid is used in the composition in an amount of 2-10% by weight of the final composition.

Preferably the acid sequestering composition includes an alkyl alkoxylate. Preferably the alkyl alkoxylate is used in the composition in an amount of 2-10% by weight of the final composition. The alkyl alkoxylate typically acts as a wetting agent. Other wetting agents could be used.

In one embodiment the container, sachet, capsule or bag contains around 1-20 ml of liquid composition, and typically around 4-10 ml of liquid composition. It will be appreciated that the volume of composition used can be varied according to the circumstances.

Typically the composition is provided at a concentration of around 0.1-10% but preferably around 1%. As a shower head and shower conduit means usually have volumes of around 100-400 ml, this typically provides a concentration of approximately 200-500 ppm when the chemical composition is diluted in water or other liquid filling the shower head and conduit means. It will be appreciated that the concentration of chemical composition can be adjusted to suit the user's systems.

Typically the chemical composition includes any or any combination of one or more foaming and/or wetting agents.

This assists in the penetration of the bio-film by the antimicrobial active component and/or other components of the chemical composition.

In one embodiment the chemical composition includes a dye and/or fragrance. The dye typically provides or forms a coloured solution when the composition is dissolved in the water flow. Thus a user can visually detect when the shower apparatus or fluid flow apparatus is being treated with the chemical composition.

In one embodiment the biocidal or sterilisation composition is used in combination with the acid sequestering composition. Preferably the acid sequestering composition is used in the applicator device before use of the biocidal composition.

According to a third aspect of the present invention there is provided an anti-microbial, a sterilisation, a biocidal or an acid sequestering applicator device for shower apparatus.

According to a fourth aspect of the present invention there is provided a composition, an anti-microbial composition, a biocidal composition, a sterilisation composition or an acid sequestering composition for use in treating, cleaning, sterilising or disinfecting one or more interior surfaces of shower apparatus or fluid flow apparatus.

According to a fifth aspect of the present invention there is provided a method of using shower sterilisation system, said system comprising shower apparatus including water supply means, a shower head and shower conduit means connecting the shower head to the water supply means, said method including the steps of locating an applicator device between the water supply means and the shower head, locating a sterilisation or biocidal composition in the applicator device and delivering said sterilisation or biocidal composition to one or more parts of said shower apparatus.

Preferably the method includes the step of allowing water to flow through the shower apparatus to cause said sterilisation or biocidal composition to be delivered to the one or more parts of the shower apparatus in use.

In a sixth aspect of the invention, there is provided a method of treating shower or fluid flow apparatus with a composition, said method including the steps of fitting an applicator device to the shower or fluid flow apparatus, disconnecting or accessing receiving means provided with or forming part of the housing, locating the composition in the receiving means, switching on the shower or fluid flow apparatus to allow a liquid or fluid to flow through at least part of the apparatus and the receiving means.

Preferably the method of treating is a cleaning, sterilising or disinfecting method.

In a further aspect of the invention, there is provided a method of cleaning or disinfecting shower apparatus, said shower apparatus including a water supply means, shower conduit means and a shower head, said method including the steps of;
  fitting an applicator device to the shower apparatus intermediate the shower conduit means and the water supply means, said applicator device provided with receiving means located in or forming part of the housing;
  disconnecting or accessing the receiving means and locating a cleaning, sterilising or disinfecting composition in the receiving means;
  switching on the shower apparatus to allow liquid to flow from the water supply means, through inlet means of the receiving means, to outlet means of the receiving means, and to the shower head via the shower conduit means.
Preferably the method includes the step of allowing the chemical composition to substantially dissolve in the water or fluid flowing through the shower or fluid flow apparatus and receiving means once it is switched on to form a chemical solution.

Preferably the chemical solution is allowed to stand or rest for a pre-determined period of time within the shower apparatus or fluid flow apparatus to allow any active ingredients of the chemical solution to take affect.

In one embodiment the predetermined time is based on the following expression:

$$\text{Biocidal 'Kill'} = f\{E.CC.CT.pH.T\}$$

Where:
The effectiveness of the biocide molecule against the target bacteria
$CC$=The contact concentration of the biocidal active component in the system
$CT$=The contact time of the formulation in the system
$pH$=The pH in the system
$T$=The temperature of the system In one embodiment the chemical solution is allowed to stand for between 5-60 minutes. Preferably the chemical solution is allowed to stand for approximately 15 minutes.

Preferably the chemical solution is flushed out or washed out from the shower apparatus or fluid flow apparatus by allowing fluid or water to flow through the apparatus again for a pre-determined period of time following the standing time.

In one embodiment the chemical composition is placed in an inner portion of the receiving means, such that liquid flows from the inner portion to the outlet means via an outer portion of the receiving means.

In one embodiment the chemical composition is provided in a container, sachet, bag or capsule that dissolves on application of liquid or water thereto.

In one embodiment any remains of the container, sachet, bag or capsule following liquid or water application is retained in the receiving means by the filtration means located between the inner and outer portions of the receiving means.

In one embodiment the shower conduit means is substantially filled up with liquid or water in which the chemical composition is substantially dissolved. Typically the shower head is also substantially filled with the chemical solution.

In an alternative embodiment the chemical solution is allowed to stand in the shower conduit means for a predetermined period of time, typically around one hour in one example. Preferably the stand time in one embodiment is 15 minutes.

Typically the shower is run hot or warm (i.e. at a temperature above normal mains water supply temperature) for a pre-determined period of time, such as for example around two minutes, before the chemical composition is added into the applicator device.

Typically the shower apparatus is flushed through with water or other liquid for around one to two minutes after the chemical solution has been allowed to stand for the predetermined period. This ensures that all traces of the treatment chemicals are removed before the shower is returned to service. This status is reached when all traces of the coloured dye and the foam generated by the wetting agents have completely disappeared from the shower spray and base.

According to further aspects of the present invention there is provided an antimicrobial shower system and a method of use thereof.

Thus, in one embodiment, the invention provides a practical approach to the in-situ sterilisation of shower apparatus via the use of a detachable or permanently attached in-line device used in conjunction with a specific chemical treatment programme designed to control microbiological activity typically in the shower conduit means and shower distribution head of the shower apparatus.

The introduction of a simple, reliable and easy to operate individual shower sterilisation system provides the opportunity for extensive, systematic control of a current potentially serious threat to public health. This system could easily be integrated into standard cleaning programmes in hospitals, hotels, sports facilities, schools, prisons, detention centres, universities and into every home in the country. The potential beneficial impact on this proven route for problematic microbiological species to threaten public health could be very significant indeed.

Specific embodiments of the invention are now described wherein:—

FIG. 4a illustrates an external side view of an applicator device according to an embodiment of the present invention and FIG. 4b illustrates a cross sectional view taken along line A-A of the applicator device in FIG. 4a.

In one aspect of the present invention there is provided a unique method for cleaning, sterilising and/or disinfecting shower apparatus, and particularly the shower hose and shower head of shower apparatus. In another aspect of the present invention there is provided a unique applicator device for allowing the cleaning or disinfecting composition to enter or be located in the shower apparatus. In a yet further aspect of the present invention there is provided a unique cleaning, sterilisation and/or disinfecting composition for use in the shower apparatus.

Applicator Device

The Applicants have designed a number of devices to allow the introduction of a biocidal or sterilisation composition and/or acidic sequestering composition into the shower apparatus. The compositions are preferably introduced into the shower hose and head of the apparatus downstream of the water control valve(s) of the apparatus.

Figure 1:
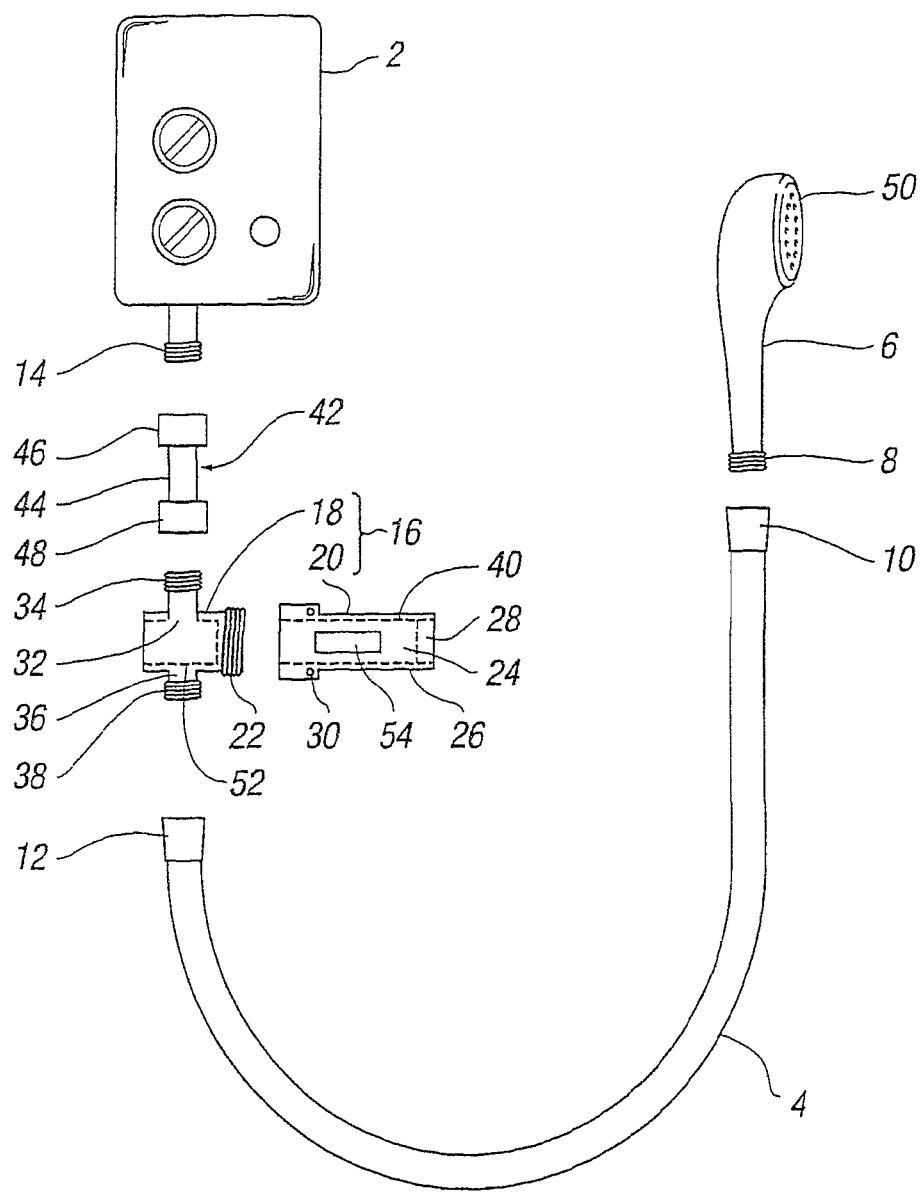
FIG. 1 illustrates an exploded schematic view of a shower system including an antimicrobial or sterilisation applicator device in accordance with an embodiment of the invention.

With reference to FIG. 1, there is illustrated shower apparatus including a water supply unit 2, a shower hose 4 and a shower head 6.

The shower head 6 is provided with a standard male screw thread connector 8 which is received by the standard female screw thread connector 10 on one end of the shower hose 4. Similarly, the other end of the shower hose is provided with a further standard female screw thread connector 12 which is adapted to fit the standard male screw thread connector 14 of the water supply unit 2.

However, according to an embodiment of the invention, the antimicrobial or sterilisation applicator device 16 is fitted intermediate the shower hose 4 and water supply unit 2.

The antimicrobial device 16 comprises a housing 18, and receiving means 20 which can be screwed on to the housing via screw thread 22 such that it extends therefrom.

The housing 18 is provided with an inlet 32 provided with a standard male screw thread connector 34 and an outlet 36 provided with a standard male screw thread connector 38.

The receiving means in this example is substantially circular in cross-section, and includes filtration means in the form of a concentric metal mesh 40, held in place by frictionally fitting to a protrusion 28. The mesh divides the receiving means into an inner portion 24 and an outer portion 26.

The inner portion 24 of the receiving means, inside the mesh 40, is large enough to hold a sachet 54 containing an antimicrobial chemical such as Lonzabac 12.100 dissolved in hexylene glycol described in more detail below. The sachet is typically made from poly(vinyl alcohol) so that it dissolves when exposed to water.

Rather than a solution, the sachet may alternatively contain a powder, which has the advantage that the sachet can be made from a thinner plastic film, which dissolves more rapidly and leaves less residue.

Thus when the receiving means 20 is connected to the housing 18, liquid entering the inlet 32 flows into the inner portion 24, dissolves the sachet to release the chemical, forming a solution which is filtered through the mesh 40 into the outer portion 26, and then flows to the outlet 36. The mesh fits over a rim 52 of an orifice leading from the inlet, and the receiving means is provided with sealing means, in the form of a rubber seal 30 in this example, to prevent leaks.

The antimicrobial applicator device in this example is provided with two male screw thread connectors 34, 38, to allow it to be connected to the water supply unit 2. An adapter 42 is also provided.

The adapter 42 comprises a tube section 44 and two standard female screw thread connectors 46, 48 located at either end thereof, thereby allowing the antimicrobial applicator device to be connected to the water supply unit 2 via the adapter 42.

Figure 2:
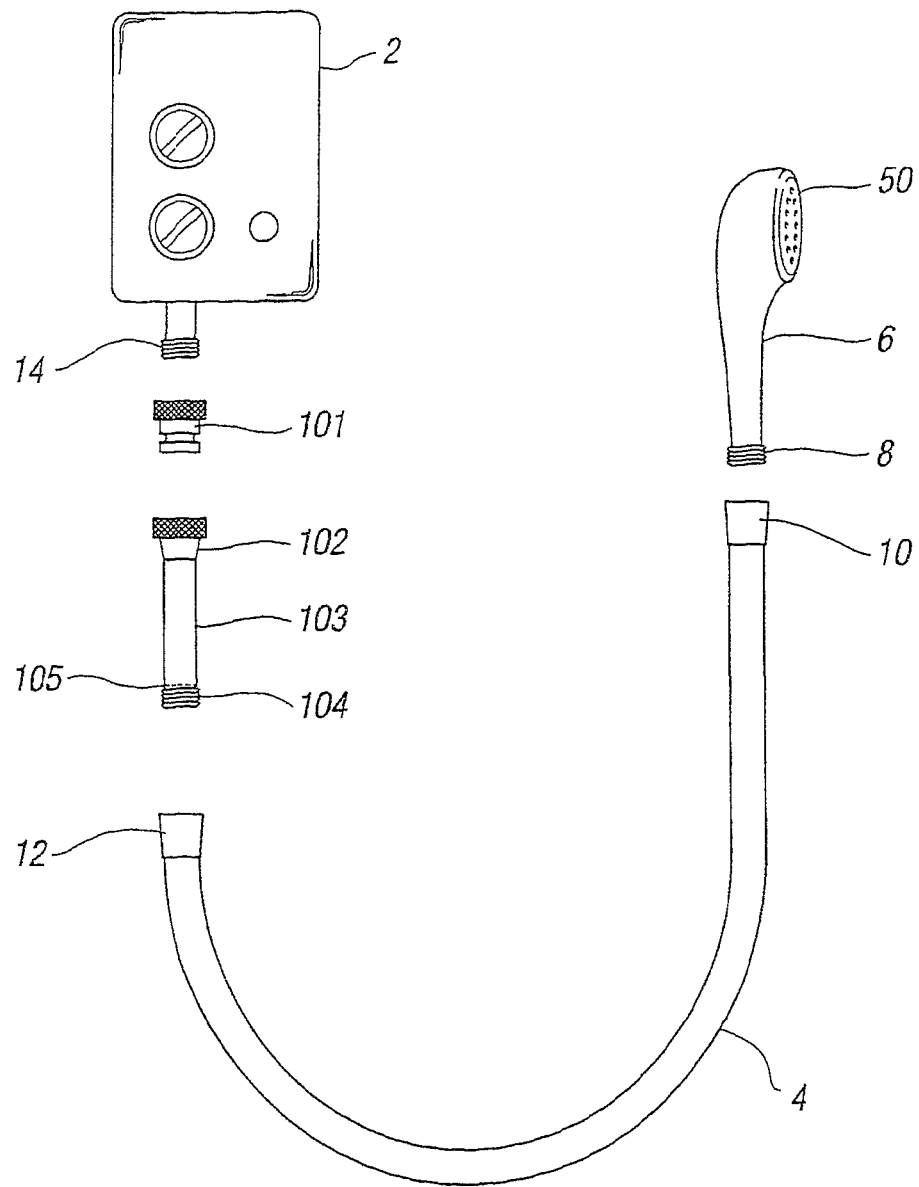
FIG. 2 illustrates an exploded schematic view of a shower system including an antimicrobial or sterilisation applicator device in accordance with a second embodiment of the invention.

With reference to FIG. 2, a second embodiment of the invention is illustrated, wherein the receiving means 103 is formed as part of the housing, in-line with the flow of water in the shower. The antimicrobial applicator device is provided with 'quick release' fittings 101, 102 allowing the device to be easily removed from the shower apparatus so that the chemical biocidal package can be placed therein above a mesh gauze 105 which acts as the filtration or screening means for filtering or retaining the PVA sachet until it dissolves completely.

Figure 3:
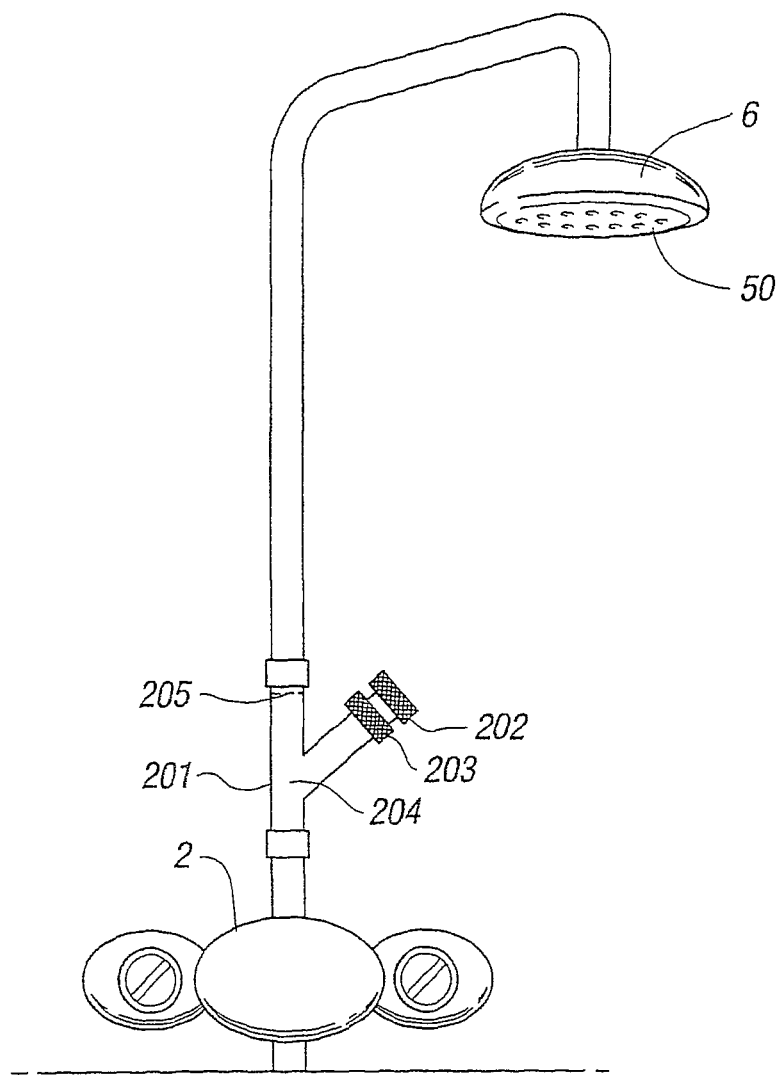
FIG. 3 illustrates a view of a shower system including an antimicrobial or sterilisation applicator device in accordance with a third embodiment of the invention.

With reference to FIG. 3, a yet further embodiment of the invention is illustrated, wherein the housing 201 is Y-shaped and fitted directly onto a rigid delivery pipe in which the flow of liquid is upwardly direction from a water supply unit located below the shower head. One branch of the Y is in-line with the pipe (i.e. concentrically arranged), whereas the other branch is provided with a quick release fitting 202 and cap 203 allowing the receiving means 204 to be accessed for placement of a chemical therein, below a mesh gauze insert 205 which filters the liquid flow.

Thus for the first time use, as shown in FIG. 1, a person disconnects the shower hose 4 from the water supply unit 2 and fits the antimicrobial applicator device 16 therebetween via the adapter 42.

The system is flushed through with hot water for one to two minutes, then a sachet 54 of biocidal composition is placed inside the mesh 40 of the receiving means 20, and the receiving means is then screwed to the housing 18.

The shower is switched on to allow water to flow through the antimicrobial applicator device 16, the water dissolving the sachet 54 to release the chemical and form a solution which flows through the mesh and to the outlet 36. The person runs the shower with the shower head in a raised position so that solution fills the hose 4, until solution comes out of the nozzles 50 of the shower head. The chemical may include a foaming agent so foam is visible at the shower head dispensing nozzles when the shower head is almost full of solution.

The cleaning solution is allowed to stand for around 15 minutes, or other predetermined period according to the user's cleaning/disinfection/sterilisation requirements.

The shower is then switched back on to flush the chemical out of the system. The chemical may be coloured so that the person can see when the liquid is free from chemical, when the water coming out of the shower head is clear.

If the sachet has not fully dissolved, it is straightforward to disconnect the receiving means, take out the filter, and wash any remaining residue off the same.

The antimicrobial applicator device does not need to be removed from the system after each use, and therefore on subsequent use the person can simply insert a new sachet of chemical and repeat the antimicrobial regime outlined above.

The HSE L8 guidelines suggest that showers are disinfected using a halogen release product such as 1-Bromo-3-chloro-5,5-dimethylhydantoin (BCDMH). However, in comparative tests it has been found that using the invention as described, wherein a solution of around 250-500 ppm Lonzabac 12.100 is created and used in the manner described above, a more effective sterilisation was achieved for a longer period than was achieved using 5 parts per million of BCDMH in the manner prescribed in the L8 recommendations.

Figure 4A:
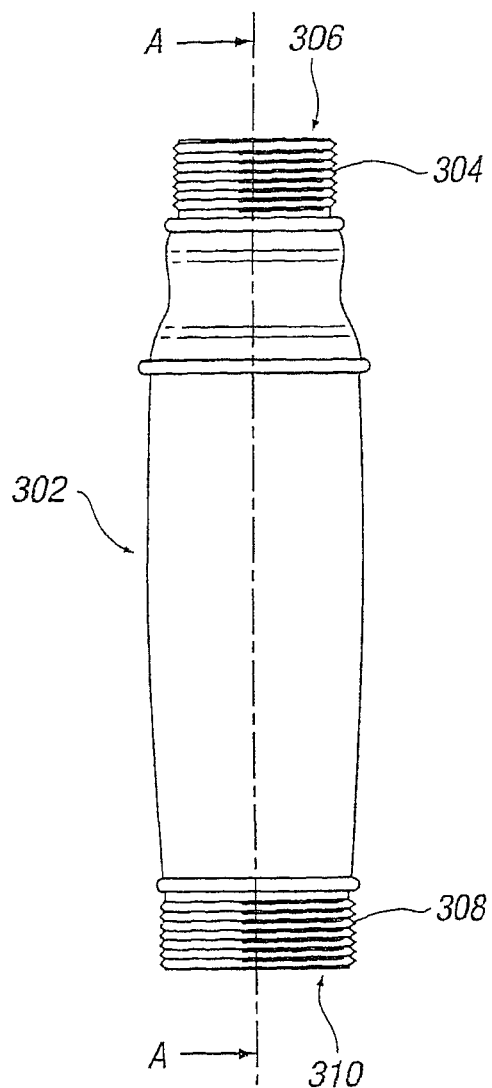
Figure 4B:
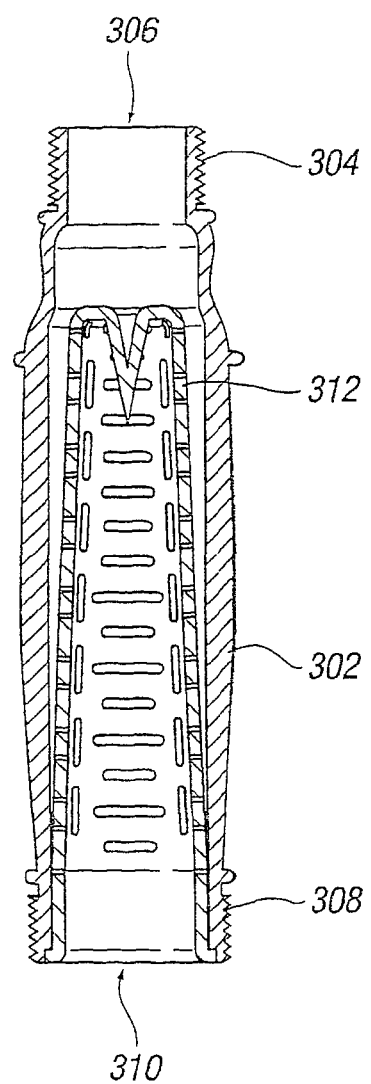

FIGS. 4a-4b illustrate an embodiment of a quick release in-line applicator device including an outer elongate sleeve housing 302 having a screw thread 308 provided at a first end 310 and a second screw thread 304 provided at a second end 306. Screw threads 304, 308 allow connection with complementary screw thread connections provided on or associated with the shower supply unit 2 and the shower hose 4, and the 'quick release' fitting 101/102 that joins thread 308 to the shower thread 14 in FIG. 2.

Receiving means in the form of a meshed basket 312 is provided in sleeve housing 302 to retain the PVA sachet containing the biocidal composition during the insertion and dissolution stage of the cleaning process. As soon as the solution of the biocide flows through the shower head, the water flow of the shower is typically stopped to allow the biocide rich solution to remain within the shower hose/head for the pre-defined contact time period. Once the pre-defined contact time has been reached, the shower is flushed through by switching the water flow in the shower back on and, in the intervening period, the remains of the sachet will have completely dissolved and can be removed from the system. It is clear when the flushing process is complete because the coloured dye contained in the composition disappears and foam from the bio-dispersants dissipates. Although the basket is removable from the sleeve housing, it is not necessary to remove it to allow insertion of the composition therein in use.

FIGS. 5a-5e illustrate a further embodiment of an in-line applicator device 402 that is located in place on the shower apparatus during fitting of the apparatus and does not require removal therefrom during a cleaning process. This applicator device 402 is particularly advantageous for use in fixed pipe or drain down shower systems where normal sterilisation is difficult without professional intervention being required to gain access to the areas of micro-biological growth and bio-film formation. The applicator device 402 is characterised by including a push fit design with a locking action to secure it in place. It is also tamper proof and no parts can be easily removed once fitted into the shower apparatus.

Applicator device 402 includes an elongate body portion 403 including push fit locking connectors 408, 410 provided at opposite ends of device 402 for secure engagement with fixed shower pipes 404, 406 respectively. An aperture 411 is defined in body portion 403 to allow the location of a PVA sachet 414 therein in use during a cleaning process. A closure sleeve 412 is slidably mounted on the outer surface of body portion 403 and is movable between a closed position, wherein aperture 411 is closed by closure sleeve 412, and an open position, wherein aperture 411 is open and access to the aperture 411 can be gained by a user. A locking nut 416 has a screw thread on an internal surface thereof for engagement with a complementary screw thread 418 provided on body portion 403 below aperture 411. Locking nut 416 can be rotated via the screw threads in one direction to hold the closure sleeve in the closed position and can be rotated in the opposite direction to allow the closure sleeve to move away from the access opening to an open position.

A non-return ball valve 420 is provided in body portion 403 towards end connector 410 to stop drain down of the pipe and shower head and allows the biocide rich solution to remain in contact with the wetted surfaces of the shower apparatus for the pre-defined sterilisation time. Filter means in the form of flat sieve members 422 are provided internally of body portion and substantially perpendicular to the direction of water flow to ensure the PVA sachet is retained in the applicator device prior to dissolution of the same.

Figure 5E:
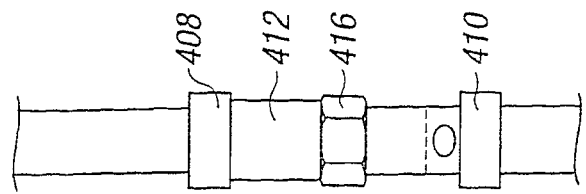
FIGS. 5a-5e illustrate a further embodiment of an in-line applicator device 402 that is located in place on the shower apparatus during fitting of the apparatus and does not require removal therefrom during a cleaning, sterilisation or disinfecting process.
Figure 5D:
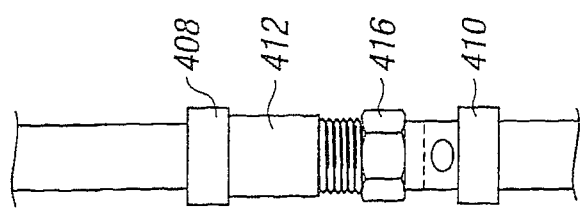
Figure 5C:
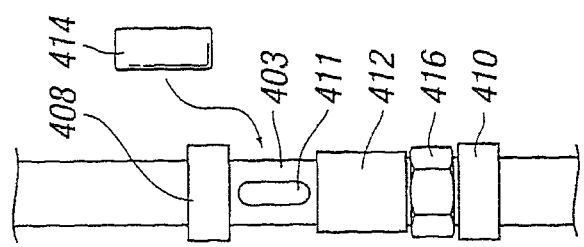
Figure 5B:
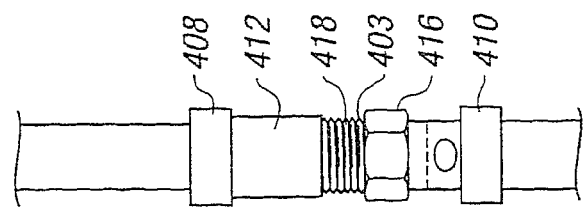
Figure 5A:
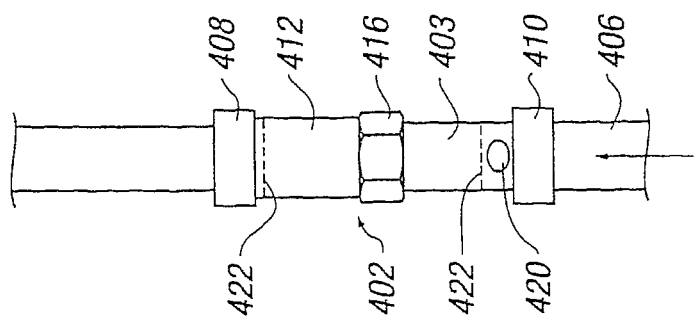

FIG. 5a shows the applicator device 402 in a closed position located between two ends of fixed pipes 404, 406. FIG. 5b shows the locking nut 416 being moved to a lowered position so that the closure sleeve 412 can be moved to an open position, as shown in FIG. 5c. Any water content present in the shower pipe and shower head are allowed to run back into the shower tray or bath via the access aperture 411. The PVA sachet containing the biocidal composition is inserted through aperture 411 in the device 402 and the closure sleeve member is then moved over the aperture 411 to the closed position to ensure no biocidal solution flows through the aperture 411 during the dissolution process, as shown in FIG. 5d. The locking nut 416 is moved back to a raised position so that the closure sleeve 412 is retained in the closed position and the device is substantially water tight, as shown in FIG. 5e.

The shower apparatus is then switched on for a few seconds to allow hot water to fill the in-line device. The water flow is then stopped for approximately 30 seconds to allow the PVA to dissolve and release the biocidal composition therefrom. The shower apparatus is then switched on and water is allowed to flow through the shower at a low rate until all the coloured dye from the composition disappears. The shower apparatus is then switched on and water is allowed to flow through the shower at a low rate until the coloured dye appears at the shower head and then the water flow is stopped. The system is then allowed to rest for approximately 15 minutes. At the end of this rest period, the shower is switched on at a relatively high flow rate to allow the system to be flushed through for several minutes and to allow any foam to disperse. The shower apparatus is then ready for normal shower use.

Figures 6A, 6B:
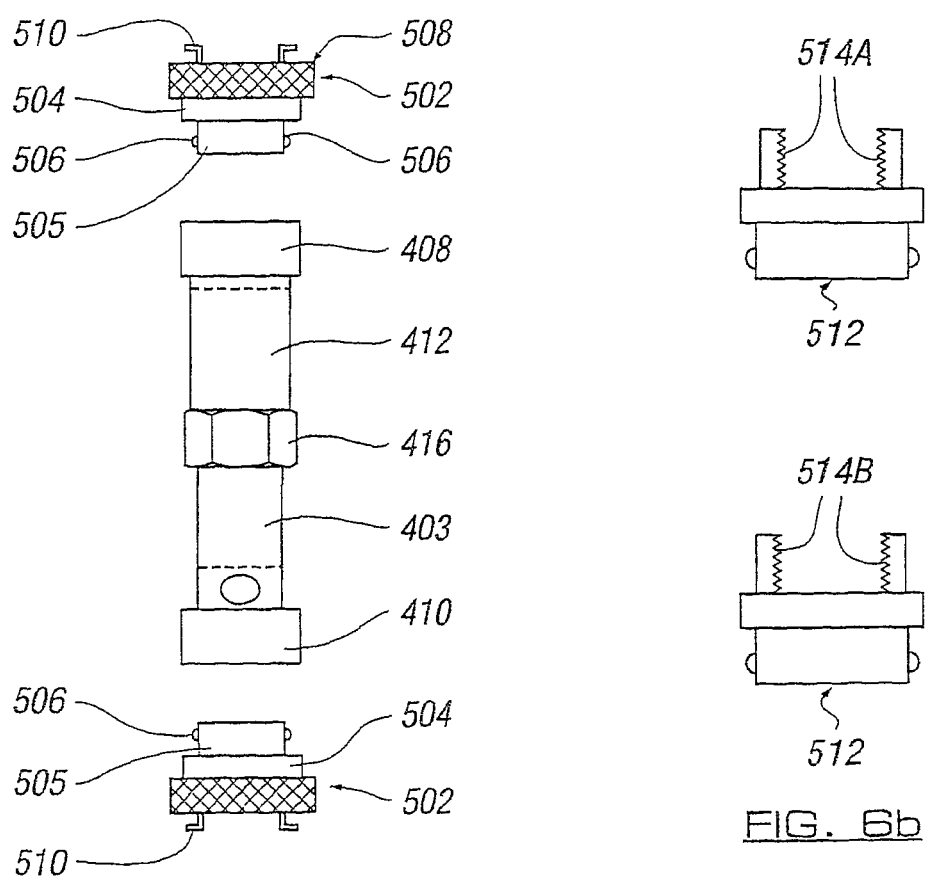
FIGS. 6a and 6b show examples of possible push fit connectors that could be used with the in-line device shown in FIGS. 5a-5e to secure the device between fixed shower pipes.

FIG. 6a shows examples of possible push fit connectors 502 that could be used with the in-line device 402 of FIGS. 5a-5e to secure the device between the fixed shower pipes 404, 406. As can be seen in FIG. 6a, the fittings 502 can be adjusted to allow the fitment of the applicator device to various sizes of fixed pipe diameters, typically 15 mm, 22 mm, 25 mm and the like.

Connector 502 includes a body portion 504 having a first end 505 with locking lugs 506 that protrude outwardly from the body portion. The locking lugs 506, or threaded connections are pushed and twisted into complementary grooves or recesses defined on the interior surface of device connectors 408, 410. On the opposite second end 508 outwardly protruding locking members 510 are provided to engage with the interior surface of the fixed pipes 404, 406.

Connector 512 is similar to connector 502 but outwardly protruding locking members 510 have been replaced by inwardly protruding engaging teeth 514. The teeth 514 A/B are designed to allow the applicator device to be inserted into the flexible shower hose as shown in FIG. 1.

Product Formulations

The method of cleaning the shower apparatus includes the application of one or two separate compositions. The first composition is in the form of a packaged biocidal or sterilisation product. The second composition is in the form of a packaged acidic sequesterant which is designed to remove the 'biofilm' and the calcium carbonate/scale that accumulates on the interior surfaces of the shower apparatus in use over time and provides a roughened surface which act as a 'key' for the growth of microbes thereon. If both compositions are used, the acidic sequesterant is used in the shower apparatus before application of the biocidal or sterilisation composition (hereinafter referred to a biocidal composition).

The fall in TVCs or "kill" of the micro-activity following use of the first biocidal product alone or following a combination of use of the first biocidal product and second acidic sequestering product is similar but the time before significant re-inoculation is extended when the combination of the first and second compositions are used. In areas of high water hardness, the potential for re-inoculation is much higher than in areas of low water hardness and therefore the benefit of using an acidic sequestering product in combination with the biocidal product is much higher.

Both the first and second compositions are characterised by meeting all regulatory requirements on a worldwide basis, are capable of being blended with other components and can be handled by non-specialist operators.

The first biocidal composition of the present invention includes a biocidal active component in the form of Bis-(3-aminopropyl)-dodecylamine which is commercially available under the trade name Lonzabac 12.100 (manufactured and distributed by Lonza AG). This biocidal composition is compatible for incorporation into a water soluble PVA sachet (i.e. is substantially or wholly non-aqueous). For example, the biocidal component can be dissolved in a non-aqueous solution such as hexylene glycol to provide compatibility with the PVA sachet.

The first biocidal composition also optionally includes one or more surface active bio-dispersants, a coloured dye (blue) and/or a fragrance.

The biocidal composition of the present invention results in a fall in TVC from a starting level of approximately $10^5$ cfu/ml to 20-500 cfu/ml.

An example of the first biocidal general formulation includes:
 1-5% N-(3-aminopropyl)-N-dodecylpropae-1,3,diamine
 2-10% Alkyl alkoxylate
 50-100% Alkylene glycol The second acidic sequestering composition includes Hydroxyl Ethylidene Di Phosphonic acid (H.E.D.P). In addition, a dispersion or wetting agent is included and a coloured dye (red). This acidic sequestering composition is compatible for incorporation into a water soluble PVA sachet (i.e. is substantially or wholly non-aqueous).

An example of the second acidic sequestering composition includes:
 2-10% phosphonic acid
 2-10% Alkyl alkoxylate
 50-100% Alkylene glycol In order to test the effectiveness of the cleaning and/or disinfecting composition of the present invention, the Applicant has devised a sampling protocol to allow reproducible data to be obtained relating to the effectiveness of the composition.

Sampling Protocol

The Applicant has found that sampling water from a running shower to monitor existing microbiological activity within a shower is difficult. This is because any water sample taken from the shower water flow is significantly influenced by the free chlorine levels in the water flowing through the shower apparatus. These free chlorine levels are typically in the region of 0.6 to 0.8 ppm. In addition, sampling of aerosols that surround the flowing water has proven to be extremely difficult to achieve with any degree of reliability or repeatability.

Thus, in order to provide an effective method of monitoring microbiological activity in a given shower system, the Applicant has devised the following approach for use in one embodiment:

1. Prior to implementation of any cleaning procedure, the shower hose is disconnected at the mixer device and the contents of the hose and head are allowed to run back into a sterile container.
2. The period of time since the shower has been used in noted.
3. The sample taken in the sterile container is tested immediately in order to minimise the potential for the microbiological activity to be influenced by a) time, b) temperature changes in transport, or c) microbiological population shifts as a result of the absence of air in the sample container or the level of food source vs the microbiological population present.
4. At least 24 hours after any treatment takes place, a repeat sample is taken as described above. The shower is routinely run for three minutes following the taking of the sample and re-connection of the hose in order to simulate normal use of the shower.
5. Subsequent samples are taken in the same way at roughly 24 hour intervals, except where a long term standing study has been carried out.

Samples taken during the early stages of the development of the present invention were analysed for Total Viable Counts using either dip slides—at remote sampling locations, or Petri-Films in local locations where laboratory facilities were available. Subsequently, extensive analyses have been carried out by third party analysts where 'full differential' analyses have been carried out. In one aspect of the present invention there is provided a method of sampling shower apparatus.

Test Results

Substantial testing, treatment and analysis of shower systems in a test facility have been carried out and a summary of the results achieved are shown below. It has been found that on standing for a period of days a typical microbiological 'count' taken on a sample of water at the beginning of the shower period can be around $10^5$ colonies per milliliter. In fact it has also been noted, as shown in the following tables, that as the ambient temperature increased during the early summer period, this level of contamination increased up to in excess of $10^6$ colonies per milliliter of shower water.

The following tables show that despite the very high levels of microbial contamination established in the shower system prior to the introduction of the treatment regime, as described above, the microbiological count in the days subsequent to the use of the chemical treatment programme produced a dramatic reduction to almost complete sterility for a number of days following the treatment. Since it is intended that the chemical treatment described is used on a weekly basis it is therefore quite conceivable that the spread of disease from this source could be completely eradicated with the adherence to a very simple and easy to administer programme.

On the basis of a typical flexible shower hose length used in UK shower systems, the biocidal composition of the present application can develop biocidal concentrations in the range of 300-600 ppm in the wetted areas of the shower hose and head.

Results using a Bis-(3-aminopropyl)-dodecylamine active in the composition of the present invention against *Legionella pneumophilia* at the Eurofins Laboratory in Milan, using the latest BS EN 13623 protocol, confirmed that the biocidal active in the composition is biocidal to *Legionella* at all concentrations in a short a contact time as 5 minutes. See Table A below.

| Concentration of Biocidal Active: | Contact time: | | | |
|---|---|---|---|---|
| | 5 Minutes: | 10 Minutes: | 15 Minutes: | 30 minutes: |
| 100 ppm | Biocidal | Biocidal | Biocidal | Biocidal |
| 200 ppm | Biocidal | Biocidal | Biocidal | Biocidal |
| 300 ppm | Biocidal | Biocidal | Biocidal | Biocidal |
| 500 ppm | Biocidal | Biocidal | Biocidal | Biocidal |

However, it is the recommendation of the Applicant that the shower system is left to soak for approximately 15 minutes before flushing the contents of the shower apparatus with water to ensure that the microbiological-activity in the apparatus has been reduced sufficiently.

TABLE 1

HADFIELD OFFICE SHOWER HEAD
HALOGEN CONTENT AND PETRIFILM MICROBIOLOGICAL ANALYSES

The object of the exercise was to determine the free and total halogen content and corresponding aerobic, yeast and mold counts of a flow of water at varying temperatures through the shower head 2 × 24 hour increments following on from the addition of a 0.5% Lonzabac 12.100 solution. 20 mls were added to the pipe/shower head which was then completely filled with water. The contents were left for 30 minutes and then flushed out. The re-calculated volume which includes the new attachment is 180 mls - giving a biocide strength of 565 ppm

| | | DATE | | | | | | | | | | | |
|---|---|---|---|---|---|---|---|---|---|---|---|---|---|
| | | 5th February 2010 | | | | 10th February 2010 | | | | 11th February 2010 | | | |
| | | Halogen Content | | Mb. Analyses | | Halogen Content | | Mb. Analyses | | Halogen Content | | Mb. Analyses | |
| Analyses | Water (°C.) | Free ppm | Total ppm | Aerobic (cols/ml) | Yeast/Mold (cols/ml) | Free ppm | Total ppm | Aerobic (cols/ml) | Yeast/Mold (cols/ml) | Free ppm | Total ppm | Aerobic (cols/ml) | Yeast/Mold (cols/ml) |
| (1) Resting (20 days) | 17 | Nil | Nil | $10^4$ to $10^5$ | 5 | Nil | 0.05 | 60 | No growth | Nil | Nil | 520 | No growth |
| (2) Shower running | 10 | 0.6 | 0.7 | 580 | No growth | 0.6 | 0.8 | No growth | No growth | 0.8 | 0.9 | 8 | No growth |
| (3) Shower running | 15 | 0.6 | 0.8 | 800 | No growth | 0.6 | 0.8 | No growth | No growth | 0.8 | 0.9 | 2 | No growth |
| (4) Shower running | 20 | 0.7 | 0.9 | 530 | No growth | 0.7 | 0.8 | No growth | No growth | 0.7 | 0.9 | No growth | No growth |
| (5) Shower running | 25 | 0.7 | 0.9 | 80 | 4 | 0.7 | 0.8 | No growth | No growth | 0.6 | 0.8 | No growth | No growth |
| (6) Shower running | 30 | 0.5 | 0.8 | 13 | No growth | 0.6 | 0.8 | 1 | No growth | 0.6 | 0.9 | No growth | No growth |
| (7) Shower running | 35 | 0.6 | 0.8 | No growth | No growth | 0.7 | 0.8 | No growth | No growth | 0.6 | 0.8 | No growth | No growth |
| (8) Shower running | 40 | 0.6 | 0.8 | 1 | No growth | 0.6 | 0.8 | 2 | No growth | 0.6 | 0.8 | 1 | No growth |
| (9) Shower running | 41 | 0.6 | 0.8 | 3 | No growth | 0.6 | 0.8 | No growth | No growth | 0.6 | 0.8 | No growth | No growth |
| | | After tests (1 to 9) completed, biocide added at 556 ppm. for a duration of 30 minutes and then flushed out. | | | | Resting temp. 15° C. 24 hours after biocide addition. | | | | Resting temp. 16° C. 48 hours after biocide addition. | | | |

TABLE 2

HADFIELD OFFICE SHOWER HEAD
HALOGEN CONTENT AND PETRIFILM MICROBIOLOGICAL ANALYSES

The object of the exercise was to determine the free and total halogen content and corresponding aerobic, yeast and mold counts of a flow of water at varying temperatures through the shower head in several periods following on from the addition of a 0.5% Lonzabac 12.100 solution. 20 mls were initially added to the pipe/shower head which was then completely filled with water. The contents were left for 30 minutes and then flushed out. The re-calculated volume which includes the new attachment is 180 mls - giving a biocide strength of 555 ppm.

DATE: $17^{th}$ February 2010

| Analyses | Water (°C.) | Halogen Content Free ppm | Halogen Content Total ppm | Mb. Analyses Aerobic (cols/ml) | Mb. Analyses Yeast/Mold (cols/ml) |
|---|---|---|---|---|---|
| (1) Resting (8 days) | 16 | Nil | Nil | $10^5$ | No growth |
| (2) Shower running | 10 | 0.8 | 0.8 | 1 | No growth |
| (3) Shower running | 15 | 0.6 | 0.8 | 3 | No growth |
| (4) Shower running | 20 | 0.6 | 0.8 | No growth | No growth |
| (5) Shower running | 25 | 0.6 | 0.8 | No growth | No growth |
| (6) Shower running | 30 | 0.6 | 0.8 | 9 | 1 yeast |
| (7) Shower running | 35 | 0.7 | 0.9 | 1 | No growth |
| (8) Shower running | 40 | 0.7 | 0.9 | No growth | No growth |
| (9) Shower running - full heat | 41 | 0.6 | 0.9 | 2 | 1 yeast |

8 days (192 hours) since biocide first added.

TABLE 3

HADFIELD OFFICE SHOWER HEAD
HALOGEN CONTENT AND PETRIFILM MICROBIOLOGICAL ANALYSES

The object of the exercise was to determine the free and total halogen content and corresponding aerobic, yeast and mold counts of a flow of water at varying temperatures through the shower head in several periods following on from the addition of an oxidising biocide - 0.05% Omnia-Stat SP (BCDMH) solution.1.8 mls (diluted to 20 mls). were added to the pipe/shower head which was then completely filled with water. The contents were left for 30 minutes and then flushed out. The re-calculated volume which includes the new attachment is 180 mls - giving a biocide strength of 5 ppm (halogen in shower head measured 4 ppm).

| | | 16th March 2010 | | | | 17th March 2010 | | | | 18th March 2010 | | | |
|---|---|---|---|---|---|---|---|---|---|---|---|---|---|
| | | Halogen Content | | Mb. Analyses | | Halogen Content | | Mb. Analyses | | Halogen Content | | Mb. Analyses | |
| Analyses | Water (°C.) | Free ppm | Total ppm | Aerobic (cols/ml) | Yeast/Mold (cols/ml) | Free ppm | Total ppm | Aerobic (cols/ml) | Yeast/Mold (cols/ml) | Free ppm | Total ppm | Aerobic (cols/ml) | Yeast/Mold (cols/ml) |
| (1) Resting (19 days) | 17 | Nil | Nil | $5 \times 10^4$ | 5 yeast | Nil | 0.05 | 480 | No growth | Nil | Nil | 2600 | 9 yeast |
| (2) Shower running | 10 | 0.7 | 0.9 | No growth | 2 yeast | 0.6 | 0.9 | No growth | No growth | 0.7 | 0.8 | 3 | 8 yeast |
| (3) Shower running | 15 | 0.7 | 0.9 | No growth | 2 yeast | 0.6 | 0.9 | 1 | No growth | 0.7 | 0.9 | 3 | 6 yeast |
| (4) Shower running | 20 | 0.6 | 0.9 | No growth | No growth | 0.6 | 0.9 | 5 | 4 yeast | 0.6 | 0.9 | 5 | 19 yeast |
| (5) Shower running | 25 | 0.7 | 0.9 | No growth | No growth | 0.7 | 0.9 | 10 | 7 yeast | 0.6 | 0.8 | 9 | No growth |
| (6) Shower running | 30 | 0.7 | 0.9 | No growth | No growth | 0.7 | 0.9 | 5 | 3 yeast | 0.6 | 0.8 | 2 | 6 yeast |
| (7) Shower running | 35 | 0.6 | 0.8 | No growth | No growth | 0.7 | 0.9 | 6 | 5 yeast | 0.7 | 0.9 | 10 | No growth |
| (8) Shower running | 40 | 0.6 | 0.8 | No growth | No growth | 0.8 | 0.9 | No growth | No growth | 0.6 | 0.8 | 6 | 10 yeast |
| (9) Shower running - full heat | 42 | 0.6 | 0.8 | No growth | No growth | 0.7 | 0.9 | No growth | No growth | 0.6 | 0.8 | No growth | 5 yeast |

After tests (1 to 9) completed, biocide added at 5 ppm. for a duration of 30 minutes and then flushed out. | Resting temp. 18° C. 24 hours after biocide addition. Full heat 43° C. | Resting temp. 17° C. 48 hours after biocide addition. Full heat 42° C.

TABLE 4

HADFIELD OFFICE SHOWER HEAD
HALOGEN CONTENT AND PETRIFILM MICROBIOLOGICAL ANALYSES
The object of the exercise was to determine the free and total halogen content and corresponding aerobic, yeast and mold counts of a flow of water at varying temperatures through the shower head in several periods following on from the addition of a 7 g form Shower Sanitiser 1 (BAC). 7 mls of neat solution - 1% active (diluted to 20 mls). were added to the pipe/shower head which was then completely filled with water. The contents were left for 30 minutes and then flushed out. The re-calculated volume which includes the new attachment is 180 mls - giving a biocide strength of 389 ppm.

| | | DATE | | | | | | | | | | | |
|---|---|---|---|---|---|---|---|---|---|---|---|---|---|
| | | 23rd March 2010 | | | | 24th March 2010 | | | | 25th March 2010 | | | |
| | | Halogen Content | | Mb. Analyses | | Halogen Content | | Mb. Analyses | | Halogen Content | | Mb. Analyses | |
| Analyses | Water (°C.) | Free ppm | Total ppm | Aerobic (cols/ml) | Yeast/Mold (cols/ml) | Free ppm | Total ppm | Aerobic (cols/ml) | Yeast/Mold (cols/ml) | Free ppm | Total ppm | Aerobic (cols/ml) | Yeast/Mold (cols/ml) |
| (1) Resting (5 days) | 19 | Nil | Nil | $10^6$ | No growth | 0.05 | 0.1 | 16 | No growth | Nil | 0.05 | 35 | No growth |
| (2) Shower running | 10 | 0.8 | 0.9 | 100 | No growth | 0.6 | 0.8 | No growth | No growth | 0.6 | 0.8 | No growth | No growth |
| (3) Shower running | 15 | 0.8 | 0.9 | 150 | No growth | 0.6 | 0.8 | No growth | No growth | 0.6 | 0.8 | No growth | No growth |
| (4) Shower running | 20 | 0.8 | 0.9 | No growth | No growth | 0.6 | 0.8 | 2 | 6 yeast | 0.6 | 0.8 | 2 | 4 yeast |
| (5) Shower running | 25 | 0.7 | 0.8 | No growth | No growth | 0.6 | 0.8 | 9 | 6 yeast | 0.6 | 0.8 | No growth | No growth |
| (6) Shower running | 30 | 0.7 | 0.8 | No growth | No growth | 0.6 | 0.8 | 1 | No growth | 0.6 | 0.8 | 1 | No growth |
| (7) Shower running | 35 | 0.7 | 0.8 | 3 | No growth | 0.6 | 0.8 | No growth | 1 yeast | 0.6 | 0.8 | 1 | No growth |
| (8) Shower running | 40 | 0.7 | 0.8 | No growth | No growth | 0.6 | 0.8 | 1 | No growth | 0.6 | 0.8 | No growth | 8 yeast |
| (9) Shower running - full heat | 42 | 0.7 | 0.8 | 1 | No growth | 0.6 | 0.8 | No growth | No growth | 0.6 | 0.8 | 2 | No growth |
| | | After tests (1 to 9) completed, biocide added at 389 ppm. for a duration of 30 mins and then flushed out (very foamy). | | | | Resting temp. 18° C. 24 hours after biocide addition. Full heat 44° C. | | | | Resting temp. 18° C. 48 hours after biocide addition. Full heat 42° C. | | | |

TABLE 5

HADFIELD OFFICE SHOWER HEAD
HALOGEN CONTENT AND PETRIFILM MICROBIOLOGICAL ANALYSES
The object of the exercise was to determine the free and total halogen content and corresponding aerobic, yeast and mold counts of a flow of water at varying temperatures through the shower head in several periods following on from the addition of a 7 g form Shower Sanitiser 1 (BAC). 7 mls of neat solution - 1% active (diluted to 20 mls). were added to the pipe/shower head which was then completely filled with water. The contents were left for 60 minutes and then flushed out. The re-calculated volume which includes the new attachment is 180 mls - giving a biocide strength of 389 ppm.

| | | DATE | | | | | | | | | | | |
|---|---|---|---|---|---|---|---|---|---|---|---|---|---|
| | | 19th April 2010 | | | | 20th April 2010 | | | | 21st April 2010 | | | |
| | | Halogen Content | | Mb. Analyses | | Halogen Content | | Mb. Analyses | | Halogen Content | | Mb. Analyses | |
| Analyses | Water (°C.) | Free ppm | Total ppm | Aerobic (cols/ml) | Yeast/Mold (cols/ml) | Free ppm | Total ppm | Aerobic (cols/ml) | Yeast/Mold (cols/ml) | Free ppm | Total ppm | Aerobic (cols/ml) | Yeast/Mold (cols/ml) |
| (1) Resting (12 days) | 19 | Nil | Nil | $10^5$ | No growth | Nil | 0.05 | No growth | No growth | Nil | 0.05 | 400 | 1 |
| (2) Shower running | 10 | 0.7 | 0.8 | 135 | No growth | 0.6 | 0.8 | 2 | No growth | 0.6 | 0.8 | No growth | No growth |
| (3) Shower running | 15 | 0.6 | 0.8 | 2 | No growth | 0.6 | 0.8 | No growth | No growth | 0.6 | 0.8 | No growth | 3 |
| (4) Shower running | 20 | 0.6 | 0.8 | No growth | No growth | 0.6 | 0.8 | 1 | No growth | 0.6 | 0.8 | 3 | No growth |
| (5) Shower running | 25 | 0.6 | 0.8 | No growth | No growth | 0.6 | 0.8 | No growth | No growth | 0.6 | 0.8 | 6 | No growth |
| (6) Shower running | 30 | 0.6 | 0.8 | 5 | No growth | 0.6 | 0.8 | No growth | No growth | 0.6 | 0.8 | 6 | No growth |
| (7) Shower running | 35 | 0.6 | 0.8 | No growth | No growth | 0.6 | 0.8 | No growth | No growth | 0.6 | 0.8 | No growth | No growth |
| (8) Shower running | 40 | 0.6 | 0.8 | 4 | No growth | 0.6 | 0.8 | 1 | No growth | 0.6 | 0.8 | 9 | No growth |

TABLE 5-continued

HADFIELD OFFICE SHOWER HEAD
HALOGEN CONTENT AND PETRIFILM MICROBIOLOGICAL ANALYSES

The object of the exercise was to determine the free and total halogen content and corresponding aerobic, yeast and mold counts of a flow of water at varying temperatures through the shower head in several periods following on from the addition of a 7 g form Shower Sanitiser 1 (BAC). 7 mls of neat solution - 1% active (diluted to 20 mls). were added to the pipe/shower head which was then completely filled with water. The contents were left for 60 minutes and then flushed out. The re-calculated volume which includes the new attachment is 180 mls - giving a biocide strength of 389 ppm.

| | | \multicolumn{4}{c}{DATE} | | | | | | | | |
|---|---|---|---|---|---|---|---|---|---|---|---|---|
| | | \multicolumn{4}{c}{19th April 2010} | \multicolumn{4}{c}{20th April 2010} | \multicolumn{4}{c}{21st April 2010} |
| | | Halogen Content | | Mb. Analyses | | Halogen Content | | Mb. Analyses | | Halogen Content | | Mb. Analyses | |
| Analyses | Water (°C.) | Free ppm | Total ppm | Aerobic (cols/ml) | Yeast/Mold (cols/ml) | Free ppm | Total ppm | Aerobic (cols/ml) | Yeast/Mold (cols/ml) | Free ppm | Total ppm | Aerobic (cols/ml) | Yeast/Mold (cols/ml) |
| (9) Shower running - full heat | 45 | 0.6 | 0.8 | No growth | No growth | 0.6 | 0.8 | No growth | No growth | 0.6 | 0.8 | 6 | No growth |
| | | \multicolumn{4}{c}{After tests (1 to 9) completed, biocide added at 389 ppm. for a duration of 60 mins and then flushed out (very foamy).} | \multicolumn{4}{c}{Resting temp. 17° C. 24 hours after biocide addition. Full heat 44° C.} | \multicolumn{4}{c}{Resting temp. 17° C. 48 hours after biocide addition. Full heat 44° C.} |

TABLE 6

HADFIELD OFFICE SHOWER HEAD
HALOGEN CONTENT AND PETRIFILM MICROBIOLOGICAL ANALYSES

The object of the exercise was to determine the aerobic, yeast and mold counts of a flow of water at varying temperatures through the shower head in several periods following on from the addition of 8.4 mls, diluted to 20 mls, of Shower Sanitiser 3 (1% active). The biocide was added to the pipe/shower head which was then completely filled with water. The contents were left for 60 minutes and then flushed out. The total volume (attachment/pipe/shower head) is 180 mls - giving a biocide strength of 467 ppm. Sample (1) 26.05.10 - Aerobic count. Dilution tubes used (100, 1000 &10000x dilution applied) to provide a more accurate count. Not required for yeast/mold plates. Subsequent tests on sample (1) after biocide addition - neat, 10x, 100x examined.

| | | \multicolumn{4}{c}{DATE} | | | | | | | | |
|---|---|---|---|---|---|---|---|---|---|---|---|---|
| | | \multicolumn{4}{c}{26th May 2010} | \multicolumn{4}{c}{27th May 2010} | \multicolumn{4}{c}{28th May 2010} |
| | | Halogen Content | | Mb. Analyses | | Halogen Content | | Mb. Analyses | | Halogen Content | | Mb. Analyses | |
| Analyses | Water (°C.) | Free ppm | Total ppm | Aerobic (cols/ml) | Yeast/Mold (cols/ml) | Free ppm | Total ppm | Aerobic (cols/ml) | Yeast/Mold (cols/ml) | Free ppm | Total ppm | Aerobic (cols/ml) | Yeast/Mold (cols/ml) |
| (1) Resting (6 days) | 20 | | | 84666 | No growth | | | 120 | No growth | | | | n/a |
| (2) Shower running | 10 | \multicolumn{4}{c}{Unable to obtain this temperature} | \multicolumn{4}{c}{Unable to obtain this temperature} | \multicolumn{4}{c}{Unable to obtain this temperature} |
| (3) Shower running | 15 | | | 6 | No growth | | | No growth | No growth | | | | n/a |
| (4) Shower running | 20 | | | 4 | No growth | | | No growth | No growth | | | | n/a |
| (5) Shower running | 25 | | | 1 | No growth | | | No growth | No growth | | | | n/a |
| (6) Shower running | 30 | | | 69 | No growth | | | 3 | No growth | | | | n/a |
| (7) Shower running | 35 | | | No growth | No growth | | | 10 | No growth | | | | n/a |
| (8) Shower running | 40 | | | 4 | 2 | | | No growth | No growth | | | | n/a |
| (9) Shower running - full heat | 45 | | | No growth | No growth | | | No growth | No growth | | | | n/a |
| | | \multicolumn{4}{c}{After tests (1 to 9) completed, biocide added at 467 ppm. for a duration of 60 mins and then flushed out (very foamy).} | \multicolumn{4}{c}{Resting temp. 19° C. 24 hours after biocide addition. Full heat 45° C.} | \multicolumn{4}{c}{Resting temp. 19° C. 48 hours after biocide addition. Full heat 45° C.} |

TABLE 7

HADFIELD OFFICE SHOWER HEAD
HALOGEN CONTENT AND PETRIFILM MICROBIOLOGICAL ANALYSES

The object of the exercise was to determine the aerobic counts of a flow of water at varying temperatures through the shower head in several periods following on from the addition of 8.4 mls, diluted to 20 mls, of Shower Sanitiser 3 (1% active). The biocide was added to the pipe/shower head which was then completely filled with water. The contents were left for 60 minutes and then flushed out for a period of 5 minutes. The total volume (attachment/pipe/shower head) is 180 mls - giving a biocide strength of 467 ppm. Sample (1) 14.06.10 - Aerobic count. Dilution tubes used (100 & 1000x dilution applied) to provide a more accurate count. Subsequent tests on sample (1) after biocide addition - neat, 10x, 100x examined.

| | | DATE | | | | | | | | | | | |
|---|---|---|---|---|---|---|---|---|---|---|---|---|---|
| | | 14th June 2010 | | | | 15th June 2010 | | | | 16th June 2010 | | | |
| | | Halogen Content | | Mb. Analyses | | Halogen Content | | Mb. Analyses | | Halogen Content | | Mb. Analyses | |
| Analyses | Water (°C.) | Free ppm | Total ppm | Aerobic (cols/ml) | Yeast/Mold (cols/ml) | Free ppm | Total ppm | Aerobic (cols/ml) | Yeast/Mold (cols/ml) | Free ppm | Total ppm | Aerobic (cols/ml) | Yeast/Mold (cols/ml) |
| (1) Resting (10 days) | 20 | | | 1360000 | | | | 980 | | | | 1047 | |
| (2) Shower running | 10 | | | Unable to obtain this temperature | | | | Unable to obtain this temperature | | | | Unable to obtain this temperature | |
| (3) Shower running | 15 | | | 4 | | | | No growth | | | | No growth | |
| (4) Shower running | 20 | | | 2 | | | | No growth | | | | No growth | |
| (5) Shower running | 25 | | | No growth | | | | No growth | | | | 34 | |
| (6) Shower running | 30 | | | 2 | | | | 82 | | | | No growth | |
| (7) Shower running | 35 | | | 2 | | | | No growth | | | | 9 | |
| (8) Shower running | 40 | | | 4 | | | | No growth | | | | 4 | |
| (9) Shower running - full heat | 45 | | | 1 | | | | No growth | | | | 2 | |
| | | After tests (1 to 9) completed, biocide added at 467 ppm. for a duration of 60 mins and then flushed for 5 mins. (very foamy). | | | | Resting temp. 20° C. 24 hours after biocide addition. Full heat 45° C. | | | | Resting temp. 20° C. 48 hours after biocide addition. Full heat 45° C. | | | |

In Table 1 it can be seen that the aerobic microbiological count at time zero was between $10^4$ and $10^5$ colonies per milliliter and that significant reductions to almost sterility were achieved in the subsequent analyses up to 48 hours following the treatment. It is worthy of note that the ambient temperature average at the time of this test was 4° C.

Table 2 shows how the microbiological activity has re-established itself 8 days after treatment with the basic biocide solution, i.e. before the inclusion of the wetting agents and other functional components.

Table 3 shows the effect of the introduction of the halogen release product BCDMH on the microbiological activity seen in the shower after 19 days resting. As can be seen, the microbiological recovery after two days is considerably greater than in the basic product results above.

Table 4 shows the impact of the inclusion of the wetting agents and other components into the final formulation. As can be seen the microbiological 'count' after 48 hours still represents a sterile environment.

In Table 5, the impact of extending the contact time of the sanitiser with the shower hose/head can be seen. Despite the fact that the level of contamination at time zero is equivalent to $10^5$ colonies per milliliter the 'count' after 24 hours is zero and after 48 hours is only 400.

In Table 6 the volume of formulated product added to the shower system was increased to 8.4 milliliters equivalent to approximately 467 ppm, and as can be seen, the microbiological count fell from 85000 colonies per milliliter at time zero to 120 colonies per milliliter after 24 hours. It is also worthy of note that the average ambient temperature at the time of testing was 8.1° C.

Table 7 shows the impact of the increase in ambient temperature on the microbiological activity at time zero. The count of $1.36 \times 10^6$ colonies per milliliter is far higher than has been seen in any of the previous tests and is probably as a direct result of the increase in ambient temperature on the microbial activity. The average ambient temperature at this time was 14"C.

Thus by adapting the shower systems to incorporate a simple in-line antimicrobial applicator device, a simple treatment with an antimicrobial chemical can be performed, and the process of shower sterilisation in whole industrial, commercial and domestic facilities can be easily achieved without the need for process disruption, the involvement of specialist contractors or the use of excessively hazardous materials.

The invention is also provided so that the cleaning treatment is quick and easy to perform on a regular basis.

Third Party Analyses

Detailed third party analyses have also been undertaken to show the effectiveness of the shower sterilisation system of the present invention. As part of this analysis, a full differential analysis of microbiological activity was completed to include aerobic bacteria, anaerobic bacteria, pseudomonads and fungi.

The samples were taken from shower apparatus in the en-suite facilities of ten bedrooms in a hotel local to the Applicant (with prior permission from the hotel owners obtained). Five of the bedrooms (Rooms 124, 133, 224, 324, 437) were treated using the biocide composition and procedure of the present invention as set out above and five of the bedrooms (Rooms 131, 231, 237, 330, 438) were treated using a conventional bleach treatment as outlined in the prior art HSE LB procedure. All the showers tested used the protocol that has been developed by the Applicant and as set out herein (i.e. the shower hose of the apparatus is disconnected from the water supply or mixer unit and the contents of the shower hose and head drained down into a sterile container). The samples were taken prior to any treatment being applied (the 'A' sample) and after standing—24 hours later (the 'C' sample). In particular, sample 'A' was taken after trickling water through the shower head and collecting the same in a sterile bottle. Sample C was taken 24 hours after each room had been treated by trickling water through the shower head and collecting the same in a sterile bottle.

Samples were taken from each sterile container and placed in sterile tubes, sealed and transported to the third party analysts.

The results below in Table 8 (also labelled Table 1) represent analyses carried out using a spiral plater technique for applying the samples to the plates.

TABLE 8

Table 1: Microbiological Analysis of Samples (as Colony Forming Unite $ml^3$)

| | Total Viable Count (FCUml2) | | | |
|---|---|---|---|---|
| | Bacterial | | | |
| Sample Details | Aerobic | Anerobic | Pseudomonads | Fungi |
| Shower Sample 124 A | $3.7 \times 10^5$ | <20 | $2.8 \times 10^5$ | <20 |
| Shower Sample 124 C | <20 | <20 | <20 | <20 |
| Shower Sample 131 A | $1.6 \times 10^5$ | $1.4 \times 10^2$ | $2.0 \times 10^4$ | <20 |
| Shower Sample 131 C | $8.0 \times 10^4$ | $2.7 \times 10^2$ | $2.2 \times 10^2$ | <20 |
| Shower Sample 133 A | $2.0 \times 10^5$ | <20 | $1.9 \times 10^5$ | <20 |
| Shower Sample 133 C | $6.1 \times 10^1$ | <20 | <20 | <20 |
| Shower Sample 224 A | $1.9 \times 10^5$ | $8.2 \times 10^1$ | $8.1 \times 10^3$ | <20 |
| Shower Sample 224 C | $8.0 \times 10^3$ | <20 | $5.7 \times 10^2$ | <20 |
| Shower Sample 231 A | $3.7 \times 10^5$ | $2.0 \times 10^1$ | $2.5 \times 10^5$ | <20 |
| Shower Sample 231 C | $3.3 \times 10^4$ | $2.0 \times 10^1$ | $1.2 \times 10^4$ | < |
| Shower Sample 237 A | $3.4 \times 10^4$ | <20 | $1.0 \times 10^2$ | <20 |
| Shower Sample 237 C | $1.1 \times 10^4$ | $2.0 \times 10^1$ | $8.2 \times 10^1$ | <20 |
| Shower Sample 324 A | $1.9 \times 10^5$ | <20 | $1.4 \times 10^5$ | <20 |
| Shower Sample 324 C | <20 | <20 | <20 | <20 |
| Shower Sample 330 A | $2.5 \times 10^5$ | $2.4 \times 10^2$ | <20 | <20 |
| Shower Sample 330 C | $3.6 \times 10^3$ | <20 | <20 | <20 |
| Shower Sample 437 A | $3.7 \times 10^5$ | <20 | $2.8 \times 10^5$ | <20 |
| Shower Sample 437 C | <20 | <20 | $2.0 \times 10^1$ | <20 |
| Shower Sample 438 A | $3.1 \times 10^4$ | <20 | $1.0 \times 10^3$ | <20 |
| Shower Sample 438 C | $1.4 \times 10^3$ | <20 | $8.2 \times 10^1$ | <20 |

The results below in Tables 9-12 represent analyses carried out using the poured plate technique for applying the samples to the plates. The TVCs were measured on the plates after 2 days for plates kept at 37° C. and after 3 days for plates kept at 22° C.

TABLE 9

Order No:
Job No:
Lab ref: 9407

FOR: Omnia-Chem Ltd
MICROBIOLOGY REPORT

Site: Hotel  Date of Sampling:- 26/04/11

| | T.V.C.- efu/ml | | | |
|---|---|---|---|---|
| Sample Point | 2 day @ 37° C. | 3 days @ 22° C. | Pseudomonas | Yeasts & Moulds |
| Room 124 A | $>10^5$ | $>10^5$ | >40,000 | 0 |
| Room 131 A | $1.9 \times 10^5$ | $7.4 \times 10^5$ | 7,600 | 0 |
| Room 133 A | $2.7 \times 10^5$ | $5.4 \times 10^5$ | ~40,0000 | 3 |
| Room 231 A | $5.5 \times 10^5$ | $1 \times 10^6$ | >40,000 | 16 |
| Room 237 A | $6.5 \times 10^4$ | $7.6 \times 10^4$ | 68 | 0 |
| Room 224 A | $3.4 \times 10^5$ | $3.7 \times 10^4$ | >40,000 | 59 |
| Room 330 A | $9.7 \times 10^4$ | $8.6 \times 10^5$ | 0 | 0 |
| Room 324 A | $3.8 \times 10^5$ | $3.4 \times 10^5$ | >40,000 | 0 |
| Room 437 A | $1 \times 10^5$ | $>10^5$ | >40,000 | 0 |
| Room 438 A | $2.5 \times 10^4$ | $4.1 \times 10^4$ | 1,080 | 0 |

TABLE 10

Order No:
Job No:
Lab ref: 9411

FOR: Omnia-Chem Ltd
MICROBIOLOGY REPORT

Site: Hotel    Date of Sampling:-27/04/11

| Sample Point | T.V.C.- efu/ml 2 day @ 37° C. | T.V.C.- efu/ml 3 day @ 22° C. | Pseudomonas Per ml | Yeasts & Moulds |
|---|---|---|---|---|
| Room 124 C | 0 | 16 | 0 | 0 |
| Room 133 C | 20 | 58 | 0 | 0 |
| Room 131 C | $9.4 \times 10^5$ | $8.2 \times 10^4$ | 320 | 0 |
| Room 224 C | 560 | 640 | 490 | 0 |
| Room 231 C | $2.3 \times 10^4$ | $2.9 \times 10^4$ | $7.5 \times 10^3$ | 0 |
| Room 327 C | $4.0 \times 10^3$ | $8.1 \times 10^2$ | 80 | 0 |
| Room 324 C | 0 | 0 | 0 | 0 |
| Room 330 C | $4.7 \times 10^4$ | $2.3 \times 10^3$ | 0 | 0 |
| Room 437 C | 56 | 132 | 32 | 0 |
| Room 438 | $6.5 \cdot 10^3$ | $1.6 \times 10^3$ | 530 | 0 |

TABLE 11

Order No:
Job No:
Lab ref: 9418

FOR: Omnia-Chem Ltd
MICROBIOLOGY REPORT

Site: Hotel    Date of Sampling:-03/05/11

| Sample Point | T.V.C. - efu/ml 2 day @ 37° C. | T.V.C. - efu/ml 3 day @ 22° C. | Pseudomonas Per ml | Yeasts & Moulds |
|---|---|---|---|---|
| Room 124 A | $5.6 \times 10^5$ | $>10^5$ | $>40,000$ | 0 |
| Room 131 A | $2.4 \times 10^5$ | $3.1 \times 10^5$ | 40 | 0 |
| Room 133 A | $1.9 \times 10^5$ | $1.4 \times 10^5$ | 8 | 5 |
| Room 224 A | $2.8 \times 10^5$ | $2.6 \times 10^3$ | $>40,000$ | 0 |
| Room 231 A | $8.4 \times 10^4$ | $8.8 \times 10^4$ | 6,100 | 0 |
| Room 237 A | 740 | 3,800 | 20 | 0 |
| Room 324 A | 132 | 220 | 68 | 0 |
| Room 330 A | $1.0 \times 10^4$ | $8.5 \times 10^4$ | 0 | 6 |
| Room 437 A | $1.6 \times 10^5$ | $>10^5$ | $>40,000$ | 1 |
| Room 438 A | $1.2 \times 10^4$ | $1.2 \times 10^4$ | 8 | 0 |

TABLE 12

Order No:
Job No:
Lab ref: 9419

FOR: Omnia-Chem Ltd
MICROBIOLOGY REPORT

Site: Hotel    Date of Sampling:-04/05/11

| Sample Point | T.V.C. - efu/ml 2 day @ 37° C. | T.V.C. - efu/ml 3 day @ 22° C. | Pseudomonas Per ml | Yeasts & Moulds |
|---|---|---|---|---|
| Room 124 C | 11 | 4,100 | 8 | 0 |
| Room 131 C | $3.0 \times 10^5$ | $2.8 \times 10^5$ | 48 | 0 |
| Room 133 C | 4 | 62 | 0 | 0 |
| Room 224 C | 16 | 14 | 12 | 0 |
| Room 231 C | 2,700 | 5,600 | 1,300 | 0 |
| Room 237 C | 1,400 | $1.9 \times 10^4$ | 156 | 0 |
| Room 324 C | 370 | 290 | 112 | 0 |
| Room 330 C | $1.7 \times 10^4$ | $4.8 \times 10^4$ | 8 | 0 |
| Room 437 C | 410 | 3,800 | 400 | 0 |
| Room 438 C | $1.4 \times 10^4$ | $1.6 \times 10^4$ | 12 | 0 |

It can be seen from tables 8-12 that the 24 our post treatment samples C taken I rooms 124, 133, 224, 324, 437, that were cleaned using the biocidal composition of the present invention in the applicator device of the present invention, show significantly reduced microbiological activity (low Total Viable Counts (TVCs). This is in contrast to the 24 hour post treatment samples C taken in rooms 131, 231, 237, 330, 438 that were cleaned using a conventional bleach composition, that show comparatively high microbiological activity (high TVCs).

In addition, the Applicants have clearly shown that the known bleaching composition and sterilisation procedure, as recommended by HSE in their L8 Protocol, do not provide the same sterilisation effectiveness for sterilising shower apparatus as the present invention. In particular, the Applicants make the following observations in relation to the known bleaching composition and procedure:

The bleach does not remove hardness scale that is present in the shower head and hose, to a greater or lesser extent depending on the water hardness levels in the local water supply. It is clear from the Applicant's tests that water hardness scale can have a significant impact on the 'key' for the development of a biofilm in the shower head and hose;

The use of a bleach soaking technique is hazardous and time consuming to apply;

It is questionable whether the required halogen residuals are established, the soaking time effectively monitored, frequencies of cleaning maintained and microbiological monitoring carried out, in any but the most carefully maintained systems;

Under the current recommendations, even though the soaking sterilisation may be carried out very effectively, the systems will re-inoculate within 7-10 days of normal use, leaving a remaining period of approximately 12 weeks before these systems are recommended for a further bleach treatment under the guidelines;

Whilst it is relatively easy to remove a flexible shower hose and head to allow the bleach soaking process to be carried out, it is almost impossible to apply this process to any fixed pipe system without significant professional intervention.

The findings of the Applicant that the formation of a biofilm in the shower apparatus can be a key factor to the effectiveness of sterilisation of the shower apparatus supports the use of an acidic sequesterant in locations where there is hard water, in addition to the biocidal composition of the present invention.

It will be appreciated by persons skilled in the art that the present invention may also include further additional modifications made to the device which does not affect the overall functioning of the device.

It will also be appreciated by persons skilled in the art that the present invention may also include further additional modifications to the formulations to include other biocidal agents, cleaning, sequestering or other materials as considered appropriate to enhance or improve the performance of the programme or to address other similar issues in similar environments.

The invention claimed is:

1. A method of using a shower sterilisation system, said system comprising shower apparatus including water supply means, a shower head and shower conduit means connecting the shower head to the water supply means, said method including the steps of locating an applicator device between the water supply means and the shower conduit means, locating a sterilisation or biocidal composition in the applicator device, switching the shower apparatus on to allow water to flow through the applicator device to allow the composition to dissolve in the water flowing through the apparatus to form a chemical solution and to deliver said sterilisation or biocidal composition to one or more parts of said shower apparatus, allowing the chemical solution to stand or rest for a pre-determined period of time within the apparatus to allow any active ingredients of the chemical solution to take effect, and switching the shower apparatus back on to flush the chemical solution out of the system.

2. A method according to claim 1 wherein the pre-determined period of time is between 5-60 minutes.

3. A method according to claim 2 wherein the pre-determined period of time is approximately 15 minutes.

4. A method according to claim 1 wherein the shower apparatus is switched on and warm or hot water is allowed to flow through the apparatus at a temperature above the mains water supply temperature for a pre-determined period of time before placing the composition in the applicator device.

5. A method according to claim 1 wherein the applicator device comprises a housing including inlet means and/or outlet means for allowing the flow of water from the shower apparatus therethrough in use, and the applicator device includes receiving means in the form of a container, basket or cavity provided with delimiting means located in or forming part of the housing, said method including the step of locating the sterilisation or biocidal composition in the container, basket or cavity.

6. A method according to claim 1 wherein the composition is contained within a container, sachet, capsule or bag formed from substantially soluble material.

7. A method according to claim 1 wherein the composition includes a non-aqueous carrier agent.

8. A method according to claim 7 wherein the non-aqueous carrier agent is or includes an alkylene glycol.

9. A method according to claim 1 wherein the biocidal composition includes N-(3-aminopropyl)-N-dodecylpropane-1,3-diamine.

10. A method according to claim 9 wherein the N-(3-aminopropyl)-N-dodecylpropane-1,3-diamine is provided in an amount of 1-5% by weight of the final composition.

11. A method according to claim 1 wherein the composition includes an alkyl alkoxylate.

12. A method according to claim 10 wherein the alkyl alkoxylate is used in an amount of 2-10% by weight of the final composition.

13. A method according to claim 1 including the step of locating an acid sequestering composition in the applicator device before the biocidal or sterilisation composition.

14. A method according to claim 13 wherein the acid sequestering composition includes phosphonic acid.

15. A method according to claim 14 wherein the phosphonic acid is used in an amount of 2-10% by weight of final composition.

* * * * *